United States Patent
Paranjape

(10) Patent No.: US 11,534,090 B2
(45) Date of Patent: *Dec. 27, 2022

(54) NON-INVASIVE PASSIVE INTERSTITIAL FLUID COLLECTOR

(71) Applicant: Georgetown University, Washington, DC (US)

(72) Inventor: Makarand Paranjape, Silver Spring, MD (US)

(73) Assignee: Georgetown University, Washington, DC (US)

( * ) Notice: Subject to any disclaimer, the term of this patent is extended or adjusted under 35 U.S.C. 154(b) by 923 days.

This patent is subject to a terminal disclaimer.

(21) Appl. No.: 16/343,060

(22) PCT Filed: Oct. 20, 2017

(86) PCT No.: PCT/US2017/057614
§ 371 (c)(1),
(2) Date: Apr. 18, 2019

(87) PCT Pub. No.: WO2018/080923
PCT Pub. Date: May 3, 2018

(65) Prior Publication Data
US 2019/0282149 A1    Sep. 19, 2019

Related U.S. Application Data

(60) Provisional application No. 62/414,448, filed on Oct. 28, 2016.

(51) Int. Cl.
*A61B 5/00* (2006.01)
*B01L 3/00* (2006.01)
(Continued)

(52) U.S. Cl.
CPC .. *A61B 5/150022* (2013.01); *A61B 5/150076* (2013.01); *A61B 5/150091* (2013.01);
(Continued)

(58) Field of Classification Search
CPC ........ A61B 5/150022; A61B 5/150076; A61B 5/150091; A61B 5/150251;
(Continued)

(56) References Cited

U.S. PATENT DOCUMENTS

| 5,200,477 A | 4/1993 | Baker et al. ................. 526/74 |
| 6,887,202 B2 | 5/2005 | Currie et al. ............... 600/309 |

(Continued)

FOREIGN PATENT DOCUMENTS

| WO | WO 2007/070093 | * 6/2007 | ............ A61B 17/43 |
| WO | WO 2017/177131 | 10/2017 | ............ B82Y 30/00 |

OTHER PUBLICATIONS

Paranjape, M. et al., A PDMS dermal patch for non-intrusive transdermal glucose sensing, Sensors and Actuators A 104 (2003) 195-204. (Year: 2003).*

(Continued)

*Primary Examiner* — Christine T Mui
(74) *Attorney, Agent, or Firm* — Bey & Cotropia PLLC; Dawn-Marie Bey

(57) ABSTRACT

A microfluidic device for non-invasively and passively accessing interstitial fluid from a patient includes a substrate containing multiple vertical micro channels therethrough, wherein at a first end of each of the multiple vertical micro channels a microheater is formed for controllably ablating a portion of dry dead skin cells to access the interstitial fluid; and wherein at a second end of each of the multiple vertical micro channels is a horizontal micro channel for receiving
(Continued)

accessed interstitial fluid from a vertical micro channel and guiding the accessed interstitial fluid to a common collection port.

14 Claims, 10 Drawing Sheets

(51) Int. Cl.
  *A61B 5/15* (2006.01)
  *A61B 5/151* (2006.01)
  *B01L 3/02* (2006.01)

(52) U.S. Cl.
  CPC .... *A61B 5/15134* (2013.01); *A61B 5/150251* (2013.01); *B01L 3/02* (2013.01); *B01L 3/502715* (2013.01); *B01L 2300/08* (2013.01); *B01L 2300/12* (2013.01); *B01L 2300/165* (2013.01); *B01L 2300/18* (2013.01)

(58) Field of Classification Search
  CPC .. B01L 3/502715; B01L 3/5027; B01L 3/502; B01L 3/50; B01L 2300/08; B01L 2300/12; B01L 2300/165; B01L 2300/18
  USPC .................................. 600/575; 422/502, 500
  See application file for complete search history.

(56) References Cited

U.S. PATENT DOCUMENTS

| | | | |
|---|---|---|---|
| 7,931,592 B2 | 4/2011 | Currie et al. | 600/309 |
| 8,568,315 B2 | 10/2013 | Currie et al. | 600/309 |
| 9,332,937 B2 | 5/2016 | Currie et al. | A61B 5/150007 |
| 10,004,434 B1 | 6/2018 | Paranjape | A61B 5/14532 |
| 2002/0010412 A1 | 1/2002 | Eppstein | 604/10 |
| 2002/0187503 A1 | 12/2002 | Harrold et al. | 435/6 |
| 2004/0099310 A1 | 5/2004 | Andersson | 137/240 |
| 2008/0121045 A1 | 5/2008 | Cole et al. | 73/861.08 |
| 2010/0303687 A1 | 12/2010 | Blaga et al. | 422/504 |
| 2011/0178380 A1 | 7/2011 | Chowdhury | 600/345 |
| 2013/0123595 A1 | 5/2013 | Currie et al. | 600/347 |
| 2013/0289374 A1 | 10/2013 | Paranjape et al. | 600/347 |
| 2014/0025000 A1 | 1/2014 | Currie et al. | 604/66 |
| 2014/0186827 A1 | 7/2014 | Pieprzyk et al. | 435/6.11 |
| 2017/0035331 A1 | 2/2017 | Paranjape et al. | A61B 5/14514 |

OTHER PUBLICATIONS

Madadi Hojjat et al 2015 Biofabrication 7 025007. (Year: 2015).*
Francioso, PDMS/Kapton Interface Plasma Treatment Effects on the Polymeric Package for a Wearable Thermoelectric Generator, dx.doi.org/10.1021/am401222p | ACS Appl. Mater. Interfaces 2013, 5, 6586-6590. (Year: 2013).*
International Search Report and Written Opinion for PCT Application No. PCT/US18/16083, dated May 8, 2018, 15 pp.
Gu, Z., "Experimental and Theoretical Study of Droplet Formation at a T-Junction With Xanthan Gum Solutions," Thesis [online], University of New South Wales, Mar. 2013 [retrieved on Mar. 16, 2018], Retrieved from the Internet: https://core.ac.uk.download/pdf/108115244.pdf, 100 pp.
Madadi, H., "Analysis and Design of a Capillary Driven Blood Plasma Separation Microfluidic Device," Thesis [online], Universitat Politecnica de Catalunya, Nov. 2013 [retrieved on Mar. 27, 2018], retrieved from the Internet: https://upcommons.upc.edu/handle/2117/96085, 99 pp.
Zulfiqar, A., et al., "Fabrication of Polyimide Based Microfluidic Channels for Biosensor Devices," Journal of Micromechanics and Microengineering, Feb. 11, 2015, vol. 25, No. 3, 9 pp., DOI: 10.1088/0960-1317/25/3/035022.
Turchinovich, et al., "The Origin, Function and Diagnostic Potential of Extracellular MicroRNA in Human Body Fluids," Frontiers in Genetics, vol. 5, Article 30, Feb. 2014.
Mielczarek, et al., "Microfluidic Blood Plasma Separation for Medical Diagnostics: Is It Worth It?," DOI: 10.1039/C6LC00833J, (Frontier) Lab Chip, 16, 3441-3448, 2016.
J. A. Loo, et al., "Comparative Human Salivary and Plasma Proteomes," J. Dent. Res. 89(10), 1016, 2010.
J. Kool, et al., "Suction Blister Fluid as a Potential Body Fluid for Biomarker Proteins," Proteomics, 7(20), 3638, 2007.
M. Brunner, et al., "Direct Assessment of Peripheral Pharmacokinetics in Humans: Comparison Between Cantharides Blister Fluid Sampling, in vivo Microdialysis and Saliva Sampling," Br. J. Clin. Pharmacol., 46(5), 425, 1998.
A.V. Romanyuk,m et al., "Collection of Analytes from Microneedle Patches," Anal. Chem. 86(21): 10520-10523, Nov. 4, 2014.
L. Ebah, "Extraction and Analysis of Interstitial Fluid, and Characterization of the Interstitial Compartment in Kidney Disease," PhD Thesis, University of Manchester, 2012.
Hotovy, et al., Gallium Arsenide Suspended Microheater for MEMS Sensor Arrays, Microsyst. Technol. 14:629-635, 2008.
Sidek, et al., "Effectd of Heater Geometry on the High Temperature Distribution on a MEMS Micro-Hotplate," $3^{rd}$ Asia Symposium on Quality Electronic Design, IEEE, 2011.
Chau, et al., "Design and Fabrication of a Quasi-Ordered Nanoporous Silicon Membrane Suitable for Thermally Induced Drug Release," J. Micromech. Microeng. 22, 085028, 14 pp. 2012.
International Search Report and Written Opinion for PCT Application No. PCT/US17/57614, dated Jan. 4, 2018, 10 pp.
U.S. Appl. No. 13/835,696, Application as filed Mar. 15, 2013 (31 pp.) (Abandoned).

* cited by examiner

FIGURE 1B – PRIOR ART
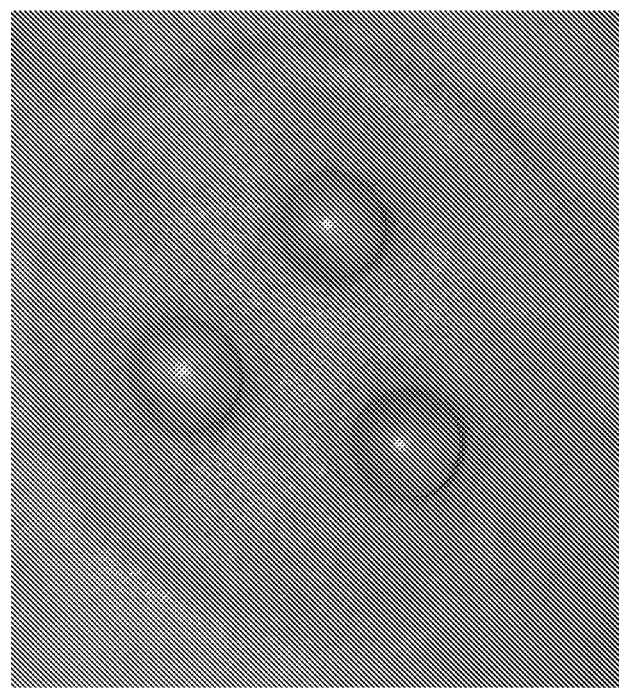
FIGURE 1A – PRIOR ART

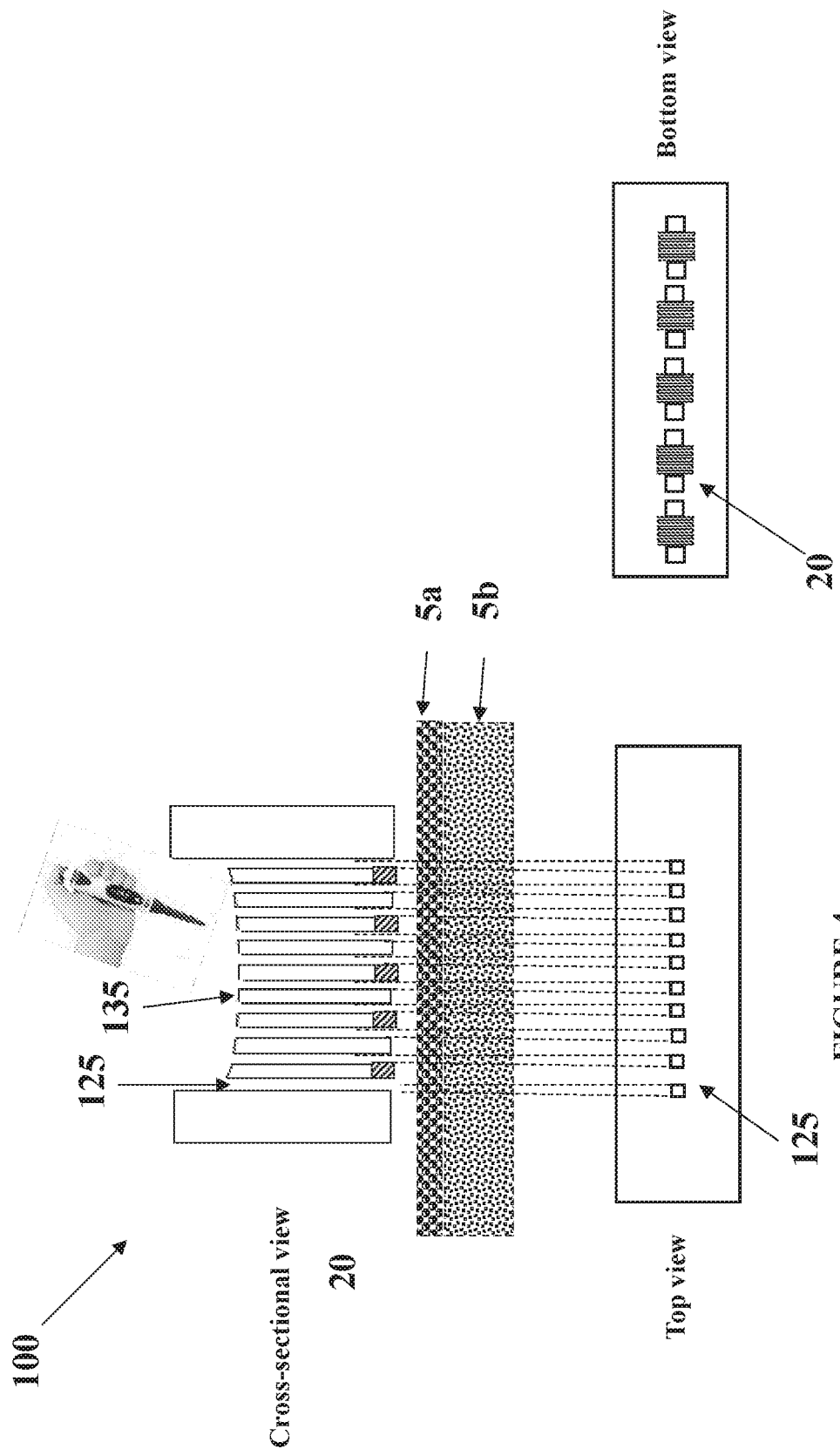

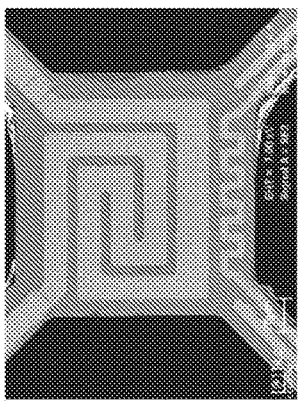
FIGURE 5b – Prior Art
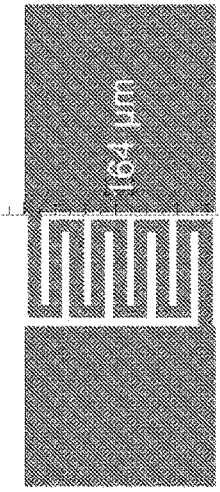
FIGURE 5c – Prior Art
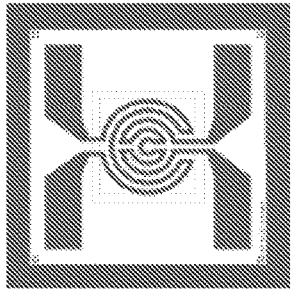
FIGURE 5i – Prior Art
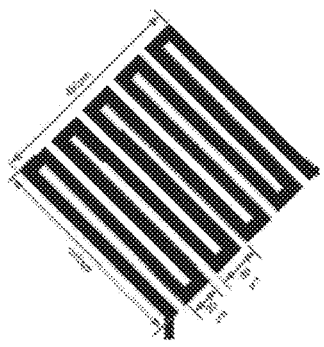
FIGURE 5a – Prior Art
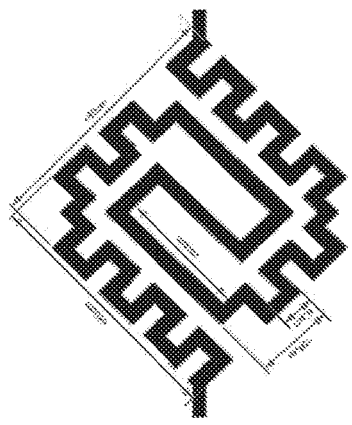
FIGURE 5e – Prior Art
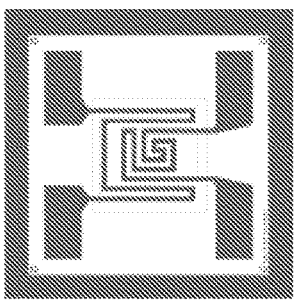
FIGURE 5h – Prior Art
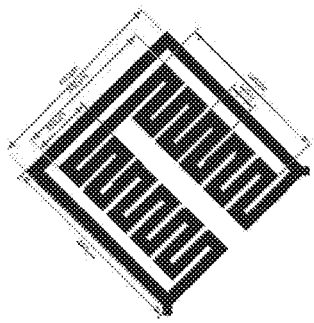
FIGURE 5d – Prior Art
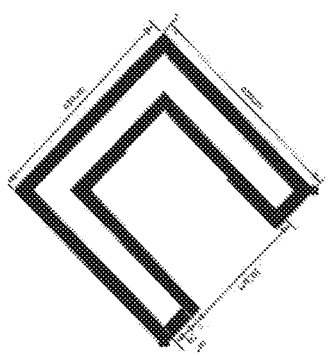
FIGURE 5g – Prior Art
FIGURE 5f – Prior Art

NON-INVASIVE PASSIVE INTERSTITIAL FLUID COLLECTOR

CROSS-REFERENCE TO RELATED APPLICATIONS

The present application claims the benefit of priority to similarly titled U.S. Provisional Patent Application Ser. No. 62/414,448 filed on Oct. 28, 2016 which is incorporated herein by reference in its entirety.

BACKGROUND

Field of the Embodiments

The present embodiments generally relate to the collection of bodily fluids for clinical testing and more particularly to devices and processes for the collection of interstitial fluid from an individual.

Description of Related Art

Blood is by far the most popular and physician-accepted choice of bodily fluid for use in clinical testing, primarily because blood is the circulating fluid that surrounds all tissue and organs and potentially collects metabolic by-products and biomarkers from both normal and diseased areas. Changes in the concentrations of specific plasma proteins have been associated with disease processes, leading to well-accepted clinical applications. The human body, however, is composed of a host of different fluids such as, urine, cerebral spinal fluid (CSF), saliva, tears, and sweat, each containing a wide variety of proteins and clinically-relevant biomarkers as discussed in J. A. Loo, et al., "Comparative Human Salivary and Plasma Proteomes", *J Dent Res.* 89(10), 1016, 2010.

Interestingly, one bodily fluid that is commonly disregarded or omitted from the list of testable bodily fluids is interstitial fluid (ISF), which also surrounds all living tissue and organs and contains constituents of the blood that are typically size excluded to being<60 kDa. Thus, clinical testing of ISF provides a completely new body fluid for diagnostic applications that has not seen any extensive use. This is mainly due to the collection methods currently available—the suction blister method described in J. Kool et al., "Suction blister fluid as a potential body fluid for biomarker proteins", *Proteomics,* 7(20), 3638, 2007 (hereafter "suction method") and the cantharide-induced skin blister method as discussed in M. Brunner, et al., "Direct assessment of peripheral pharmacokinetics in humans: comparison between cantharides blister fluid sampling, in vivo microdialysis and saliva sampling", *Br J Pharmacol.,* 46(5), 425, 1998 (hereafter "blister method"), both interestingly considered as non-invasive.

Referring to prior art FIGS. 1A and 1B, the suction method involves the application of vacuum suction on the skin surface for at least 2 hours, resulting in the epidermis slowly becoming detached from the underlying dermis. The resulting induced blister fills with interstitial fluid that can be collected by piercing the blister with a syringe needle to draw the ISF. A variant of using a suction pump is to raise suction blisters using syringes, which can take more than 2 hours to produce. Although these procedures are considered as being painless, at worst causing itching and discomfort, the resulting wounds typically heal in 7 to 10 days without forming any scars. However, some subjects can develop hyperpigmentation at the wound sites that can last for months or longer.

The blister method for obtaining ISF samples relies on the toxic reaction of cantharide on the skin to generate sub-epidermally located skin blisters. Cantharides are blistering agents made from the powdered, dried bodies of *Lytta vesicatoria*, or the blister beetle. The principle component of cantharide is cantharidin, the blistering agent shown to potentially cause adverse effects. For this reason, it has been included in a list of "problem drugs". However, when compounded properly and applied in the clinic topically by medical personnel familiar with its effects and uses, cantharidin can be safely and effectively used to treat some benign skin lesions like warts. In order to collect ISF, the cantharides are impregnated onto a dermal patch and adhered to the skin for 12 hours. The resulting blister fluid can be aspirated into a syringe by puncturing the blister with a fine needle, similar to the collection strategy used in the suction method.

An even more invasive approach to collect ISF is to use micro-needles to draw the INF as described in the article by A. V. Romanyuk et al. entitled "Collection of Analytes from Microneedle Patches," *Anal Chem.* 2014 Nov. 4; 86(21): 10520-10523 ("Romanyuk et al.").

Obviously, the methods above used to harvest interstitial fluid are uncomfortable, time-consuming, and intrusive, and a blood draw would likely seem to provide a simpler course.

Accordingly, a less invasive and more efficient device and process for collecting ISF would be welcome by both patients and the clinical community.

SUMMARY OF EMBODIMENTS

A first exemplary embodiment includes a microfluidic device for non-invasively and passively accessing interstitial fluid from an individual, the microfluidic device including: a substrate containing multiple vertical micro channels therethrough, Wherein at a first end of each of the multiple vertical micro channels a microheater is formed for controllably ablating a portion of the dry dead skin cells to access the interstitial fluid; and further wherein at a second end of each of the multiple vertical micro channels is a horizontal micro channel for receiving accessed interstitial fluid from a vertical micro channel and guiding the accessed interstitial fluid to a common collection port.

A second exemplary embodiment includes a microfluidic device for non-invasively and passively accessing interstitial fluid from an individual, the microfluidic device including: a first layer formed of a polyimide such as KAPTON®; a second layer formed of poly(dimethylsiloxane) (PDMS), wherein the first and second layer are bonded together; an array of vertical microchannels formed through the first and second layer; and an electrically controllable microheater formed at a Kapton end of each of the vertical microchannels.

BRIEF DESCRIPTION OF FIGURES

FIGS. 1A and 1B illustrate the results of prior art blister formation techniques used to collect ISF;

FIGS. 5a to 5i illustrate exemplary prior art micro-heater configurations for use with one or more of the exemplary embodiments described herein;

DETAILED DESCRIPTION

Current knowledge of the physiological and pathophysiological composition of interstitial fluid is mainly based on blood studies due to the relative ease of obtaining a blood sample. The study of the true composition of interstitial fluid is hindered by the relative difficulty in extracting or sampling it. Such difficulties are identified and discussed in articles by L. Ebah, "Extraction and Analysis of Interstitial Fluid, and Characterization of the Interstitial Compartment in Kidney Disease", PhD Thesis, University of Manchester, 2012 and Romanyuk et al., both of which are incorporated herein by reference.

Figure 2A:
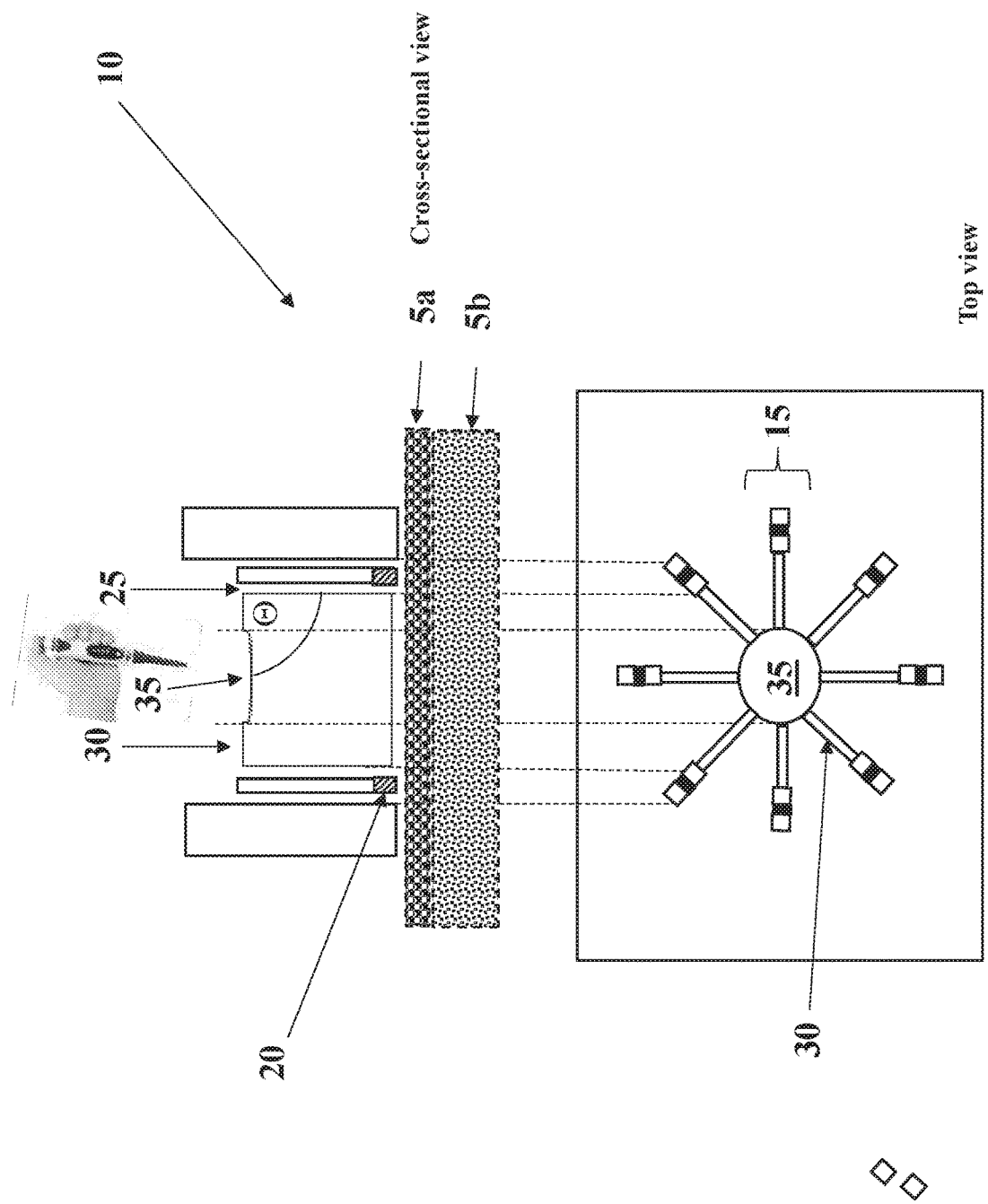
FIGS. 2a and 2b illustrate an exemplary embodiment of the present invention wherein a microheater and microchannel configuration with a collection reservoir which may be used to collect BF.

The present embodiments outline a simple, effective, and time efficient way to painlessly collect ISF from a patient. This device may be utilized to assess the presence of certain biomarkers in ISF using standard clinical methods including, but not limited to, mass spectrometry, liquid chromatography, etc. The device utilizes microfluidic technology to help in the transfer process of ISF from the skin surface to a collection port for subsequent aspiration by pipetting (see FIG. 2). The ISF originates using, for example, thermal ablation micro-heaters 20, situated on the device surface, or inset therein that will be placed in contact with the top layer of the skin containing dry, dead skin cells, or stratum corneum, 5a. Multiple micro-heaters 20 may be activated simultaneously or in succession in order to harvest larger volumes of ISF, as needed, from lower layers of skin 5b. FIG. 2a illustrates cross-sectional and top views of an exemplary system 10 having 8 individual ablation/collection sites 15. At each collection site 15, there is a single micro-heater 20 flanked by two vertical micro-channels 30. The microheaters and channels may be in various shapes and configurations, including rectangular, square, circular or combinations thereof. The dimensions of the vertical micro-channels may be on the order of approximately 50-100 microns per side. The spatial separation distance between sites 15 can be determined, and varied, based on whether dermal trauma is indicated. The ISF resulting from the thermal ablation is transported through hydrophilic vertical micro-channels 25 by capillary action, and connected to approximately horizontal micro-channels 30 oriented substantially in the plane of the device surface and ending at a common collection port 35. Each vertical micro-channel 25 with a corresponding substantially horizontal micro-channel 30 is formed in the substrate with angle Θ therebetween. These generally planar micro-channels can be arranged in any way that maximizes collection, such as with a spoke-like configuration illustrated in FIG. 2a. In FIG. 3, the approximately horizontal micro-channels are oriented so as to be slightly inclined towards the central collection port 35 such that angle Θ is less than 90 degrees. In both configurations, the collection port 35 may be indented slightly to pool the ISF from the horizontal channels 30, although such an indentation is not required.

Figure 4C:
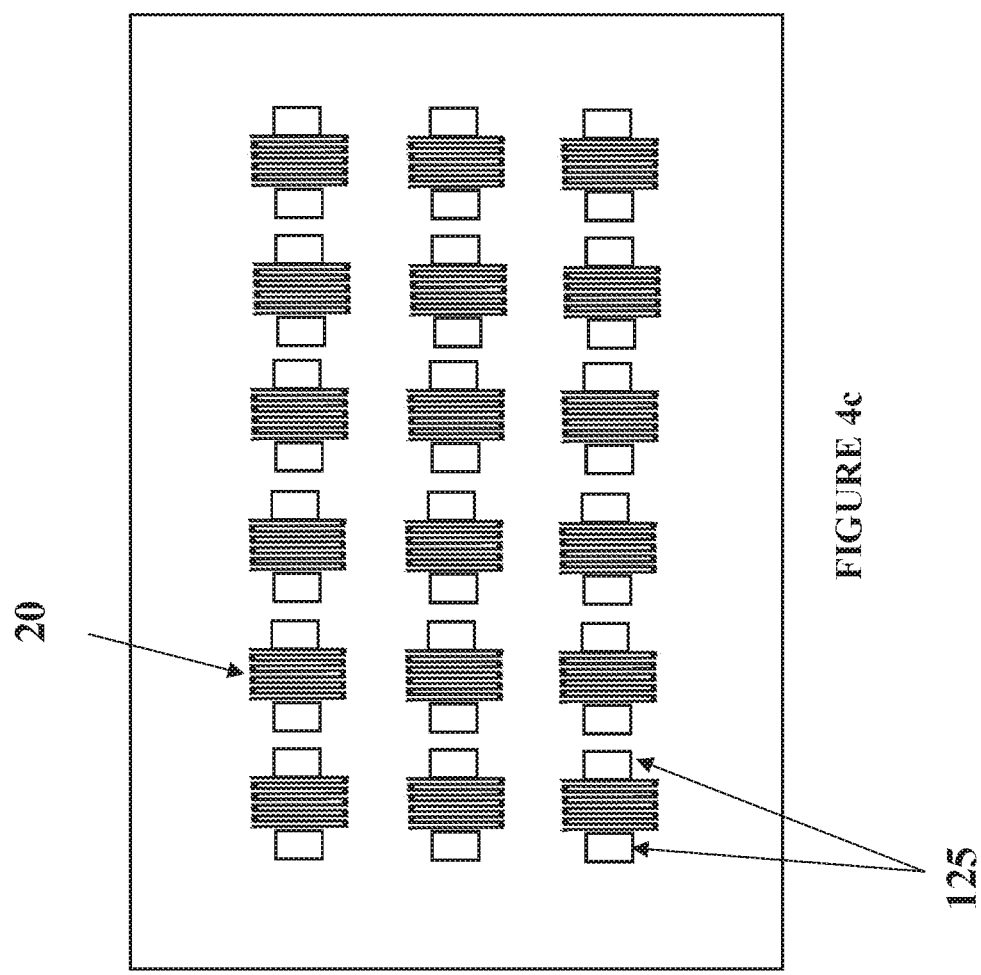
FIGS. 4a and 4b illustrate a second exemplary embodiment of the present invention wherein a microheater and microchannel configuration with a collection reservoir which may be used to collected ISF.

Alternatively, FIGS. 4a-4c illustrate a system 100 having different collection geometries wherein multiple vertical micro-channels 125 simply terminate at a central collection area 135 and the ISF can be extracted from the central collection area 135 for analysis. The number of collection channels feeding the central collection area and the arrangement thereof is not limited. FIGS. 4a and 4b show a configuration having a line of 10 separate collection channels 125 whereas FIG. 4c shows a bottom view of a 12×3 array of collection channels 125. In FIG. 4a, the collection area 135 is shown as being formed so as to resemble a trough or bowl to better collect the ISF for extraction. This trough or bowl configuration of the central collection area 135 is not required.

The thermal ablation micro-heaters 20 function to ablate a microscopic portion of the stratum corneum containing dry, dead skin cells, the topmost layer of skin 5a, so that the interstitium, part of lower layer 5b, can be exposed, releasing ISF. The micro-heaters 20 are in close proximity to the skin surface, together with electrical components that control current to the micro-heaters 20. Each micro-heater preferably comprises a pair of electrodes connected by a conductive pathway that is arranged, either by the use of a resistive material or by a serpentine conductive pathway, to provide sufficient resistance to the flow of electricity such that an effective amount of heat is produced so as to locally ablate an appropriate portion of the stratum corneum. Electrical connections may also be provided to each of the two electrodes to connect the micro-heating unit to a controller that controls the application of an electrical current source to the electrodes, thus providing for individualized control of heating on a per micro-heater 20, per collection site 15 basis. In operation, the micro-heater 20 is pulsed with a suitable alternating or direct current to provide local ablation. Control of the duration and intensity of the heating pulse is preferably carried out to effect ablation of the desired area and depth. The micro-ablation preferably occurs in a confined volume of the stratum corneum. By way of example only, an area having the dimensions of approximately 50 μm×50 μm×40 μm may be suitable for collection of an adequate amount of ISF. Alternative embodiments are contemplated wherein the individual micro-heaters may be for single-use, as compared to multiple use, such that when the individual micro-heater is used, the heating circuit is "blown" and may not be used again.

Additional details regarding micro-heater configurations and details which may be used with one or more of the embodiments herein may be found in commonly owned and similarly titled U.S. Pat. Nos. 6,887,202, 7,931,592, 8,568, 315 and 9,332,937, which are incorporated herein by reference.

Figure 6:
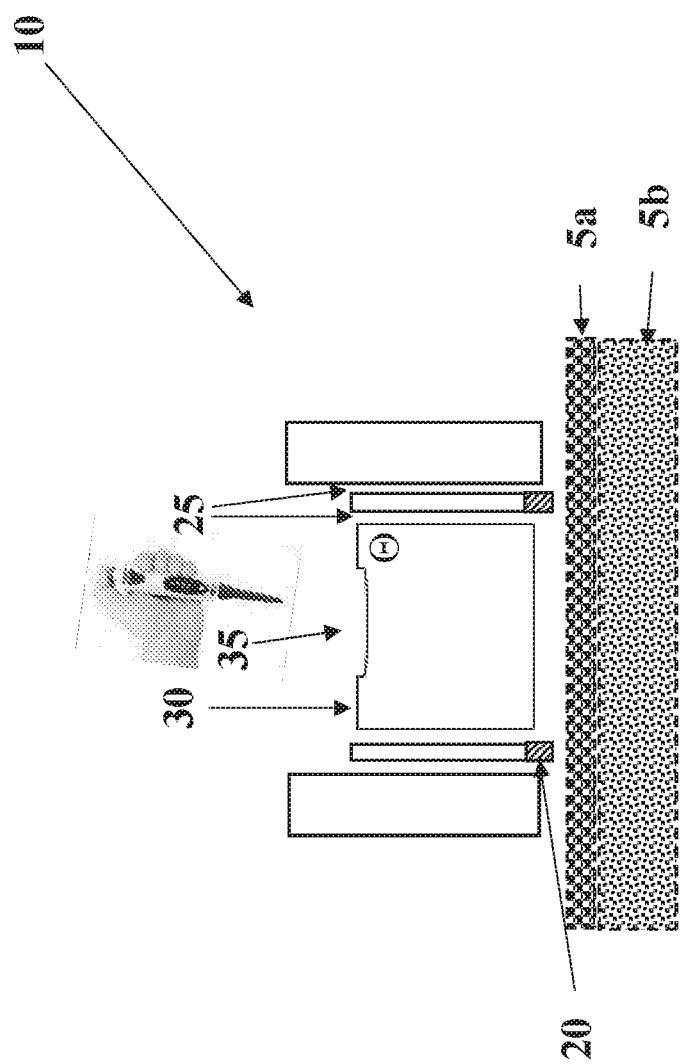
FIG. 6 illustrates an alternative micro-heater placement configuration within one or more of the exemplary embodiments described herein.

Exemplary prior art micro-heater configurations are shown in FIGS. 5a-5i. Although rectangular, serpentine micro-heaters are shown in the figures, the embodiments are not so limited. Further, variations to the placement of the micro-heaters with respect to the opening of the vertical microchannels is not limited to the configuration shown in the figures. That is, alternative configurations contemplate that instead of being inset within the substrate, some portion of the micro-heater may be layered on the substrate and thus be protruding therefrom as shown in FIG. 6. Further, it is contemplated that the suspension may be achieved from a single side of the opening. Fabrication techniques and materials for suspending the heater across the opening of each vertical micro-channel are known to those skilled in the art. The following articles discuss suspended microheaters and the substance thereof is incorporated herein by reference: Hotovy et al., Gallium arsenide suspended microheater for MEMS sensor arrays, Microsyst Technol (2008) 14:629-635; Sidek et al., Effect of Heater Geometry on the High Temperature Distribution on a MEMS Micro-hotplate, $3^{rd}$ Asia Symposium on Quality Electronic Design, IEEE 2011; Chau et al., Design and fabrication of a quasi-ordered nanoporous silicon membrane suitable for thermally induced drug release, J. Micromech. Microeng. 22 (2012) 085028 (14pp).

Figure 2B:
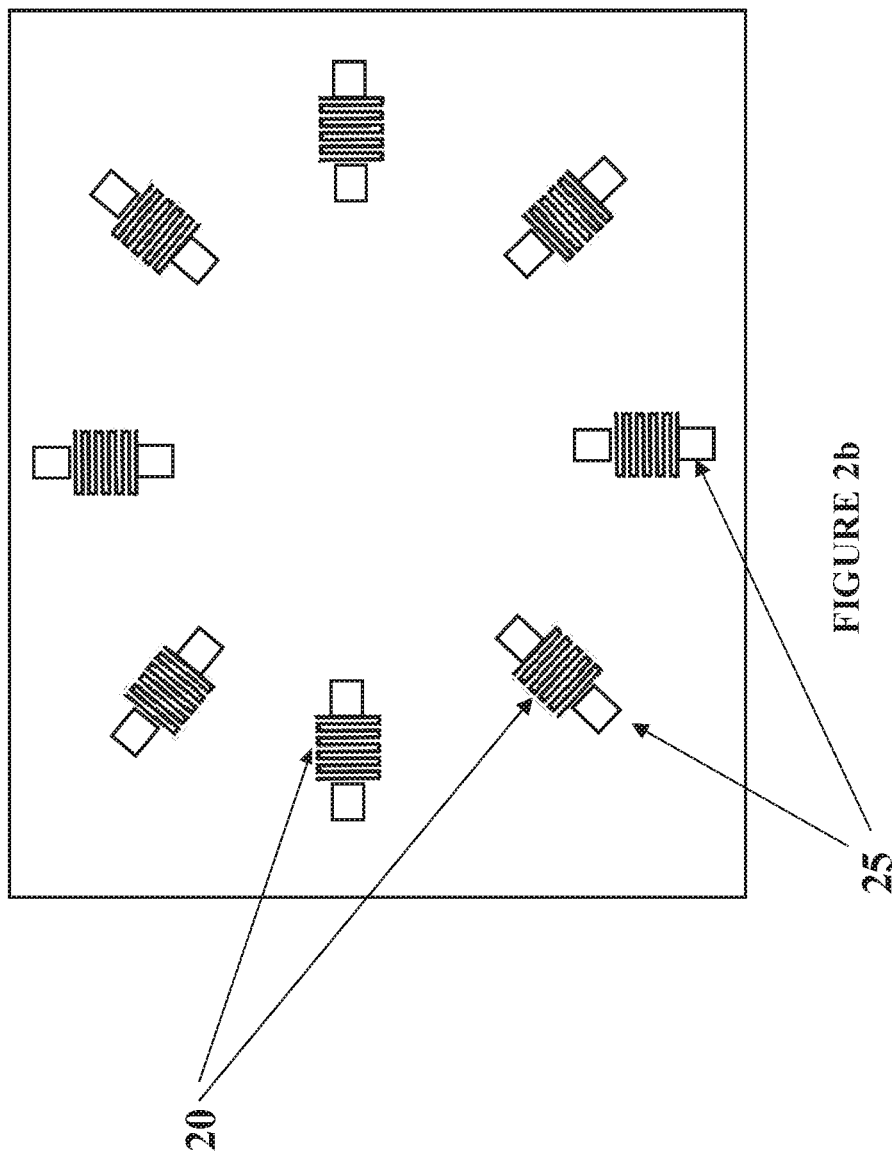
Figure 3:
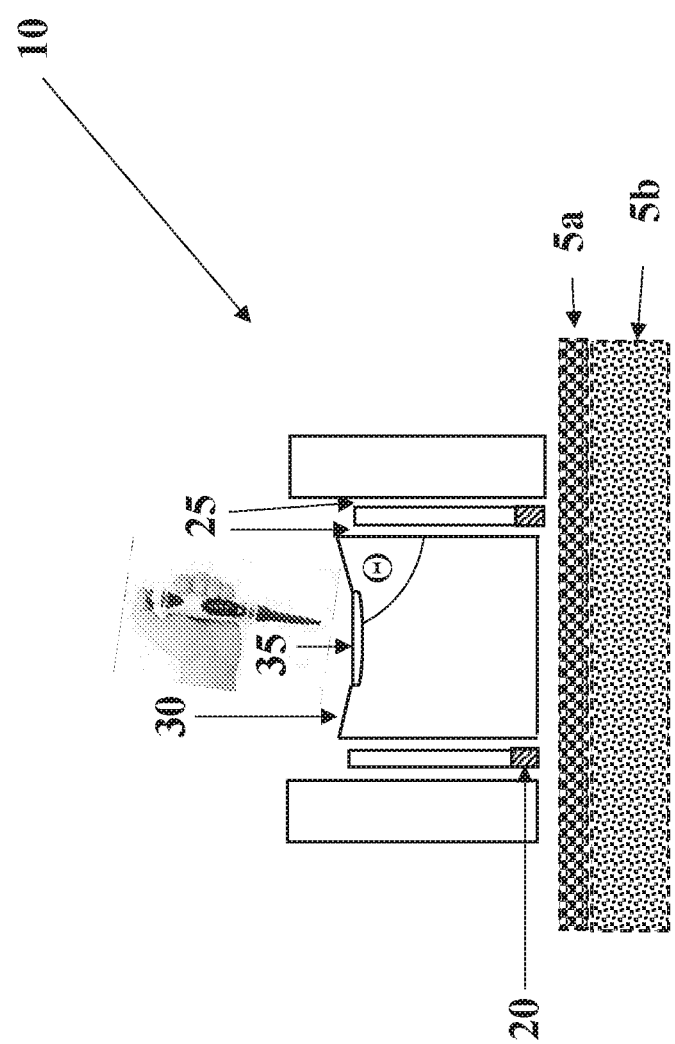
FIG. 3 illustrates a first exemplary embodiment of the present invention wherein a microheater and microchannel configuration with a collection reservoir which may be used to collect ISF.
Figure 7:
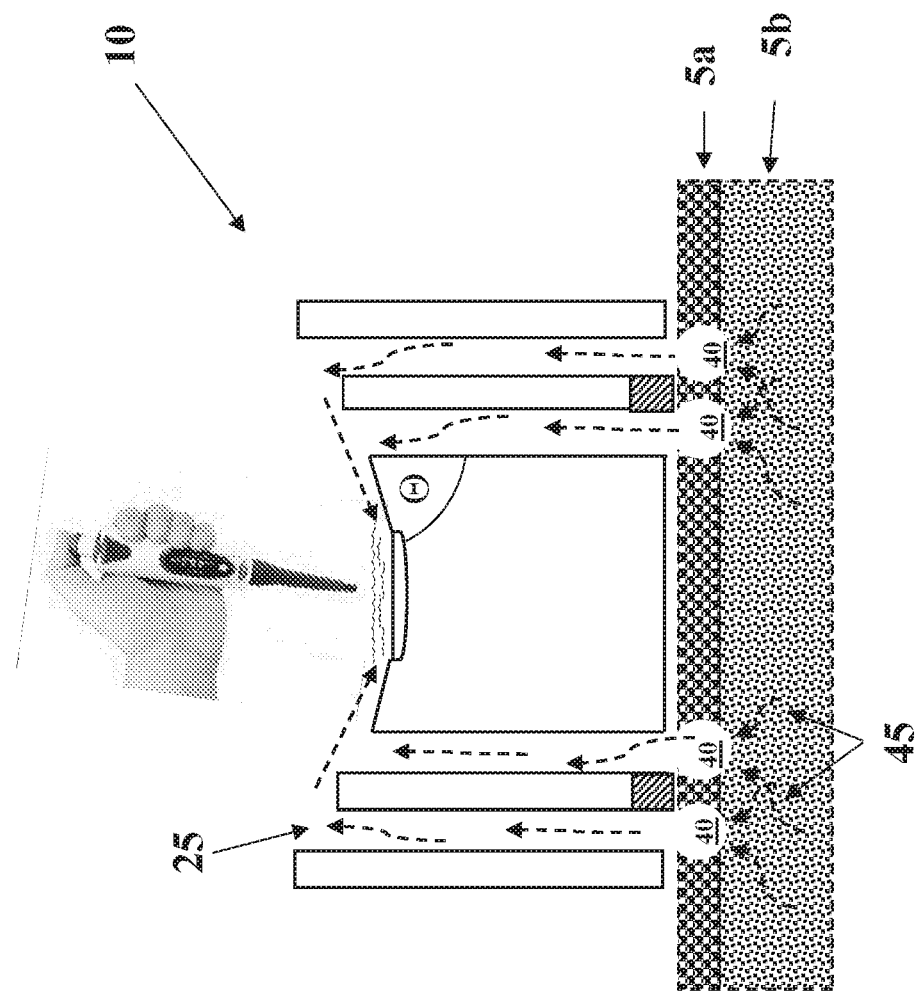
FIG. 7 illustrates the embodiment of FIGS. 2a and 2b during use.

Using the embodiment from FIGS. 2a-2b as an example, FIG. 7 illustrates the configuration after the stratum corneum 5a has been ablated by micro-heaters 20 to form micropores 40 therein and access the BF 45, which is shown by broken arrows. The ISF is drawn up through the vertical microchannels 25 by capillary action.

For ease of fabrication and processing, the representative structure may be formed in poly(dimethylsiloxane) (PDMS) or KAPTON®(polymide), but it is understood by one skilled in the art that this is not the only material that can be used. PDMS channels may be formed using a molding process with high aspect ratio photoresist (SU-8) while KAPTON® can be chemically etched using patterned protective layers of metallic films. Laser processing may also be used for both PDMS and KAPTON®. In an alternative embodiment, the final device may be comprised of PDMS bonded with KAPTON®, where KAPTON® is the layer containing the microheaters and in contact with the skin, while the PDMS serves to transport the ISF upwards. Since PDMS is inherently hydrophobic, it is treated to render it hydrophilic. This may be accomplished by adding a nonionic organosilicone surfactant such as SILWET®-77Silwet-77.

Figure 8:
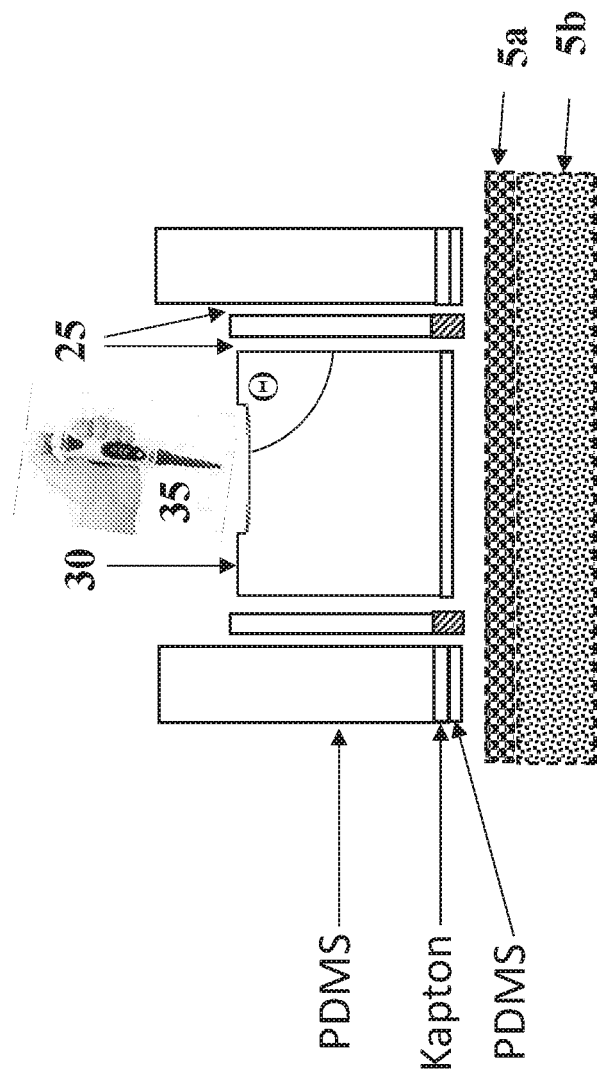
FIG. 8 illustrates an alternative embodiment of the device using combinations of materials.

Alternatively, as shown in FIG. 8 an additional thin PDMS layer with openings for the microheater and microchannels can be added to the KAPTON® layer to provide a hydrophobic surface to aid in guiding ISF to the vertical microchannels from the skin. The result is that the microheaters 20 are very slightly recessed from the main surface of the device as shown, but are still well within heating reach of the skin. The thin PDMS layer may be on the order of 100 microns thick.

The following patents and patent applications, which are co-owned by the Applicant and include an overlapping inventor with the present application, are incorporated herein by reference in their entireties and variations to the present embodiments in accordance with one or more teachings therein are considered to be within the scope of these embodiments: U.S. Pat. No. 6,887,202, titled "Systems and Methods For Monitoring Health and Delivering Drugs Transdermally," U.S. Pat. No. 7,931,592, titled "Systems and Methods For Monitoring Health and Delivering Drugs Transdermally," U.S. Pat. No. 8,568,315, titled "Systems and Methods For Monitoring Health and Delivering Drugs Transdermally," U.S. Pat. No. 9,332,937, titled "Systems and Methods For Monitoring Health and Delivering Drugs Transdermally," U.S. Pub. No. 2013-0289374, titled "Electrochemical Transdermal Glucose Measurement System Including Microheaters and Process For Forming," U.S. application Ser. No. 13/835,696, titled "Microfluidic Systems For Electrochemical Transdermal Glucose Sensing Using a Paper-Based or Other Wicking Substrate," U.S. application Ser. No. 13/834,199, titled "Microfluidic Systems For Electrochemical Transdermal Analyte Sensing Using a Capillary-Located Electrode," and U.S. application Ser. No. 15/226,475, titled "Apparatus and Method For Delivery of Antimicrobial During a Transdermal Sampling and Delivery Process."

The invention claimed is:

1. A microfluidic device for non-invasively and passively accessing interstitial fluid from an individual, the microfluidic device comprising:
   a substrate comprising layers of both poly(dimethylsiloxane) (PDMS) and polyimide, the substrate containing multiple vertical microchannels therethrough, wherein at a first end of each of the multiple vertical microchannels a microheater is formed for controllably ablating a portion of dry dead skin cells to access the interstitial fluid; and
   further wherein at a second end of each of the multiple vertical microchannels is a horizontal microchannel for receiving accessed interstitial fluid from at least one of the vertical microchannels and guiding the accessed interstitial fluid to a common collection port, wherein an angle between each of the multiple vertical microchannels and a corresponding horizontal microchannel is less than 90 degrees.

2. The microfluidic device of claim 1, wherein the first end of each of the multiple vertical microchannels containing a microheater is formed of polyimide and the second end of each of the multiple vertical microchannels, each horizontal microchannel and the common collection port are PDMS.

3. The microfluidic device of claim 2, wherein the PDMS is treated to make it hydrophilic.

4. The microfluidic device of claim 3, wherein the PDMS is treated by adding a nonionic organosilicone surfactant.

5. The microfluidic device of claim 1, wherein the multiple vertical microchannels, each with a horizontal microchannel, and the common collection port are arranged in a spoke and wheel configuration, wherein each horizontal microchannel ends at the common collection port.

6. The microfluidic device of claim 1, wherein each microheater is formed in-line with the first end of each of the multiple vertical microchannels at a circumference of an opening at the first end of each of the multiple vertical microchannels.

7. The microfluidic device of claim 1, wherein each microheater is formed in-line with the first end of each of the multiple vertical microchannels and at least a portion thereof is suspended across an opening at the first end of each of the multiple vertical microchannels.

8. The microfluidic device of claim 1, wherein each microheater is formed so as to protrude from the first end of each of the multiple vertical microchannels at a circumference of an opening at the first end of each of the multiple vertical microchannels.

9. A microfluidic device for non-invasively and passively accessing interstitial fluid from an individual, the microfluidic device comprising:
   a first layer formed of polyimide;
   a second layer formed of poly(dimethylsiloxane) (PDMS), wherein the first and second layer are bonded together;
   an array of vertical microchannels formed through the first and second layer;
   at least one electrically controllable microheater formed at a polyimide end of each of the vertical microchannels; and a horizontal microchannel fluidly connected at a PDMS end of each vertical microchannel in the array of vertical microchannels for directing the interstitial fluid to a collection port, wherein an angle between each of vertical microchannel and a corresponding horizontal microchannel is less than 90 degrees.

10. The microfluidic device of claim 9, wherein the PDMS is treated to make it hydrophilic.

11. The microfluidic device of claim 10, wherein the PDMS is treated by adding a nonionic organosilicone surfactant thereto.

12. The microfluidic device of claim 9, further comprising a third layer formed of PDMS over a portion of the polyimide layer, but excluding each of the at least one electrically controllable microheater and each of the vertical microchannels.

13. The microfluidic device of claim 9, wherein at least a portion of the electrically controllable microheaters is suspended across an opening at the polyimide end of each of the vertical microchannels.

14. The microfluidic device of claim 9, wherein the least one electrically controllable microheater is formed so as to protrude from the polyimide end of each of the vertical microchannels at a circumference of an opening at the polyimide end of each of the vertical microchannels.

* * * * *